United States Patent [19]

Labrie

[11] Patent Number: 4,659,695

[45] Date of Patent: Apr. 21, 1987

[54] METHOD OF TREATMENT OF PROSTATE CANCER

[76] Inventor: Fernand Labrie, 2735 boul Liegeois, St-Foy, Québec, G1W 1Z9, Canada

[21] Appl. No.: 699,711

[22] Filed: Feb. 8, 1985

[51] Int. Cl.$^4$ .............................................. A61K 37/24
[52] U.S. Cl. ........................................ 514/15; 514/800
[58] Field of Search ................................... 514/15, 800

[56] References Cited

PUBLICATIONS

Chem. Abstr. vol. 93, (1980) 161786.
Chem. Abstr. vol. 95, (1981) 1980552.
Chem. Abstr. vol. 103, (1985) 81710b.
Chem. Abstr. vol. 103, (1985) 16943r.
Chem. Abstr. vol. 103, (1985) 17095c.
Chem. Abstr. vol. 103, (1985) 17072t.
Chem. Abstr. vol. 103, (1985) 65288g.
Chem. Abstr. vol. 103 (1985) 65277.
Chem. Abstr. vol. 102, (1985) 125663.
Chem. Abstr. vol. 102, (1985) 198133.
Chem. Abstr. vol. 101 (1984) 33528.
Chem. Abstr. vol. 101, (1984) 66091.
Chem. Abstr. vol. 101, (1984) 66370.
Chem. Abstr. vol. 101 (1984) 164017.
Chem. Abstr. vol. 100, (1984) 45370.
Chem. Abstr. vol. 100, (1984) 203971.
Chem. Abstr. vol. 100, (1984) 97001.
Chem. Abstr. vol. 97, (1982) 33431.
Chem. Abstr. vol. 99, (1983) 134104.
Chem. Abstr. vol. 96 (1982) 1121.
Chem. Abstr. vol. 96, (1982) 97844.
Chem. Abstr. vol. 96, (1982) 136731.

*Primary Examiner*—Delbert R. Phillips
*Attorney, Agent, or Firm*—Thomas D. Hoffman; Gerald S. Rosen

[57] ABSTRACT

A method of treatment of prostate cancer in susceptible male animals including humans whose testicular hormonal secretions are blocked by surgical or chemical means, e.g., by use of an LH-RH agonist, e.g., [D-Trp$^6$, des-Gly-NH$_2^{10}$]LH-RH ethylamide which comprises administering an antiandrogen, e.g., flutamide in association with at least one inhibitor of sex steroid biosynthesis, e.g., aminoglutethimide and/or ketoconazole. Pharmaceutical compositions useful for such treatment and three, four and five component kits containing such compositions are also disclosed.

44 Claims, No Drawings

METHOD OF TREATMENT OF PROSTATE CANCER

BACKGROUND OF THE INVENTION

This invention relates to a method of treatment of prostate cancer in warm-blooded male animals including humans in need of such treatment using a combination therapy comprising administering an antiandrogen in association with an inhibitor of sex steroid biosynthesis to such animals after the hormone output of their testes has been blocked by surgical or chemical means. The invention also includes pharmaceutical compositions useful for such treatment. In its most preferred aspect, this invention relates to treatment of hormone-dependent prostate cancer in warm-blooded male animals by parenterally administering an LH-RH agonist or antagonist in association with orally administering an antiandrogen and orally administering at least one inhibitor of sex steroid biosynthesis.

While various investigators have been studying hormone-dependent breast and prostate cancer, none have proposed the combination therapy of this invention.

A. V. Schally et al., Cancer Treatment Reports, 68, (No. 1) 281-289 (1984), summarize the results of animal and clinical studies on growth inhibition of hormone-dependent mammary and prostate tumors by use of analogues of luteinizing hormone-releasing hormones, the so-called LH-RH agonists and suggest that LH-RH analogs and/or antagonists may have potential for treating breast cancer.

T. W. Redding and A. V. Schally, Pro. Natl. Acad. Sci. USA, 80, 1459-1462 (1983), disclose inhibition of prostate tumor growth in rats by chronic use of an LH-RH agonist, [D-Trp$^6$]LH-RH.

In U.S. Pat. No. 4,329,364, it is disclosed that the antiandrogen, 4'-nitro-3'-trifluoromethyl isobutyranilide may be used for treatment of prostatic cancer.

In U.S. Pat. No. 4,472,382, it disclosed that prostate adenocarcinoma, benign prostate hypertrophy and hormone-dependent mammary tumors may be treated with various LH-RH agonists and that prostate adenocarcinoma and benign hypertrophy may be treated by use of various LH-RH agonists and an antiandrogen. However, there is no suggestion or disclosure of the present invention.

Some clinical improvement in men with prostate cancer by use of the two LH-RH agonists, Buserelin and Leuprolide, is also reported by N. Faure et at. at pages 337-350 and by R. J. Santen et al. at pages 351-364, respectively, *LH- RH and its Analogs - A New Class of Contraceptive and Therapeutic Agents* (B. H. Vickery and J. J. Nestor, Jr., and E. S. E. Hafez, eds) Lancester, MTP Press, (1984).

R. Santen et al., The Journal of Steroid Biochemistry, Volume 20, No 6B, at page 1375 (1984), disclose that use of ketoconazole in combination with chronic administration of Leuprolide in rodents decreased basal and Leuprolide stimulated testosterone levels.

D. Kerle et al., The Journal of Steroid Biochemistry, Volume 20, No 6B, at page 1395 (1984) disclose that the combined use of a LH-RH analogue and ketoconazole produced objective responses in some prostate cancer patients who have relapsed or failed to respond to treatment with a LH-RH analogue alone.

F. Labrie et al., The Prostate, 4, 579-594 (1983), disclose that use of a combination therapy of an LH-RH agonist (Buserelin) and an antiandrogen (Anandron) to treat advanced prostate cancer in previously untreated patients effects simultaneous elimination of androgens of both testicular and adrenal origin.

F. Labrie et al., J. Steroid Biochem., 19, 99-1007 (1983), disclose the treatment of prostate cancer by the combined administration of an LH-RH agonist and an antiandrogen. Labrie et al. disclose animal and clinical data in support of the proposition that the combined LH-RH/antiandrogen treatment neutralizes the stimulatory influence of all androgens on the development and growth of androgen-dependent prostatic cancer.

F. Labrie et al., Abstracts of 7th International Congress of Endrocrinology, Excerpta Medica (1984) at page 98 discloses that treatment of prostate cancer patients with LH-RH agonists alone causes a transient increase in serum androgen levels lasting for 5 to 15 days before castration levels are reached. While F. Labrie et al. recommends that orchiectomy, estrogen and LH-RH agonists alone should not be further used for treatment of prostate cancer in the absence of a pure antiandrogen, there still is a need for a method of treatment of prostate cancer that effects more complete androgen blockage at the start as well as during the full period of treatment.

BRIEF DESCRIPTION OF THE INVENTION

In one aspect, the invention provides a method of treating prostate cancer in a warm-blooded male animal including humans in need of such treatment which comprises blocking the testicular hormonal secretions of said animal by surgical or chemical means and administering to said animal a therapeutically effective amount of an antiandrogen in association with at least one inhibitor of sex steroid biosynthesis, or pharmaceutical compositions thereof. By simultaneously blocking sex-steroids (androgens and estrogens of testicular and adrenal origin) production and/or action, the present invention provides a method of inhibiting the growth of hormone-sensitive prostate carcinomas in warm-blooded male animals having such carcinomas.

In another respect, the present invention provides a method of treating prostate cancer in a castrated warm-blooded male animal, i.e., such an animal whose testicular hormonal secretions have been previously blocked by surgical or chemical means, which comprises administering to said animal a therapeutically effective amount of an association of an antiandrogen and at least one inhibitor of sex steroid biosynthesis, or pharmaceutical compositions thereof.

In male mammals, the removal of testicular androgens may be achieved by surgical castration (orchiectomy) but preferably the secretion of androgens from the testes is blocked by chemical castration by administering to warm-blooded male animal, an effective amount of an LH-RH agonist or antagonist. In a preferred aspect, the present invention provides a method of treating prostate cancer in a warm-blooded male animal having prostate cancer, which comprises administering to said animal therapeutically effective amounts of an LH-RH agonist or antagonist in association with an antiandrogen and at least one inhibitor of sex steroid biosynthesis, or pharmaceutical compositions thereof.

In its preferred aspect, the LH-RH agonist is administered parenterally (subcutaneously intramuscularly) and the antiandrogen and the inhibitor or inhibitors of sex steroid biosynthesis are each administered orally.

The invention also provides kits or single packages combining three, four and five separate preferred pharmaceutical compositions useful in treating prostate cancer. The three component kit provides the antiandrogen oral pharmaceutical composition, the LH-RH agonist or LH-RH antagonist parenteral composition and the sex steroid biosynthesis inhibitor oral pharmaceutical composition; the four component kit provides the LH-RH agonist or LH-RH antagonist parenteral pharmaceutical composition, the antiandrogen oral pharmaceutical composition and, the adrenal sex steroid biosynthesis inhibitor oral pharmaceutical composition and the hydrocortisone oral pharmaceutical composition; and the five component kit provides the LH-RH agonist or LH-RH antagonist parenteral pharmaceutical composition, the antiandrogen oral pharmaceutical composition and the testicular sex steroid biosynthesis inhibitor oral pharmaceutical composition, the adrenal sex steroid biosynthesis inhibitor oral pharmaceutical composition and the hydrocortisone oral pharmaceutical composition.

DETAILED DESCRIPTION OF THE INVENTION

In one preferred aspect, the present invention provides an effective method of treating prostate cancer in warm-blooded male animals in need of such treatment by administering a LH-RH agonist or antagonist in association with an antiandrogen and an inhibitor of sex steroid biosynthesis of testicular origin or pharmaceutical compositions thereof in amounts sufficient to inhibit prostate cancer. By use of an inhibitor of testicular sex steroid biosynthesis in association with an antiandrogen and a LH-RH agonist or antagonist more complete androgen blockage is effected at an earlier stage in the treatment of prostate cancer than achieved by prior art methods.

In another preferred aspect, the use of an LH-RH agonist or antagonist in association with an antiandrogen and two inhibitors of sex steroid biosynthesis, e.g. an inhibitor of adrenal sex steroid biosynthesis such as aminoglutethimide and an inhibitor of testicular sex steroid biosynthesis such as ketoconazole, produced almost complete blockage of testicular steroid secretion while simultaneously blocking the precursor sex steroids (androgens and estrogens) of adrenal origin at an early stage of the treatment. While such complete, blockage of androgen secretion and/or action has not been achieved by prior art methods, such complete, blockage can be achieved and maintained throughout the period of treatment in accordance with the present invention. These active compounds can be administered together or in any order as discussed hereinafter. To assist in determining the effect of the treatment, blood plasma concentrations of the adrenal androgens and estrogens and prostate size are measured. Lowered concentrations of sex steroids and reduction in prostate size are indicative of successful treatment, e.g. inhibition of prostatic cancer cell growth. The concentrations of adrenal androgens and estrogens such as dehydroepiandrosterone (DHEA), DHEA-sulfate (DHEAS), androst-5-ene-3$\beta$,17$\beta$-diol ($\Delta^5$-diol) and, the estrogen, 17$\beta$-estradiol (E$_2$) are measured by standard methods well known to those skilled in the art, see for example F. Labrie et al., The Prostate, 4, 579–594 (1983).

Prostatic size is measured by rectal examination and by transrectal ultrasonography. Objective assessment of the effect of the treatment is also measured by standard physical methods well known to those skilled in the art, e.g., bone scanning, X-ray, skeletal survey, intravenous pyelography, CAT-scan and physical examination. The response criteria for prostate developed by the U.S.A. National Prostate Cancer Project (The Prostate, 1, 375–382) may also be used.

The use of therapeutically effective amounts of the inhibitor of testicular sex steroid biosynthesis such as ketoconazole in association with the antiandrogen and the LH-RH agonist or LH-RH antagonist in accordance with the present invention effectively surpresses the serum sex steroid levels, especially serum testosterone and dihydrotestosterone concentrations stimulated by treatment with LH-RH agonist at the start of the treatment even in the presence of an antiandrogen.

While a LH-RH agonist or a LH-RH antagonist may be used in one preferred aspect of the present invention, the use of a LH-RH agonist is more preferred.

By the term "LH-RH agonist" is meant synthetic analogues of the natural luteinizing hormone-releasing hormone (LH-RH), a decapeptide of the structure:

L-pyroglutamyl-L-histidyl-L-tryptophyl-L-seryl-L-tyrosyl-glycyl-L-leucyl-L-arginyl-L-prolylglycyl-NH$_2$ Typical suitable LH-RH agonists include nonapeptides and decapeptides represented by the formula:

L-pyroglutamyl-L-histidyl-L-tryptophyl-L-seryl-L-tyrosyl-X-Y-L-arginyl-L-prolyl-Z wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl or N-methyl-D-alanyl and Y is L-leucyl, D-leucyl, N$^\alpha$-methyl-D-leucyl, N$^\alpha$-methyl-L-leucyl or D-alanyl and wherein Z is glycyl-NHR$_1$ or NHR$_1$ wherein R$_1$ is H, lower alkyl or lower haloalkyl. Lower alkyl includes straight or branched chain alkyls having 1 to 6 carbon atoms, e.g., methyl, ethyl, propyl, pentyl or hexyls, iso-butyl, neopentyl and the like. Haloloweralkyl includes straight and branched chain alkyls of 1 to 6 carbon atoms having a halogen substituent, e.g., —CF$_3$,—CH$_2$CF$_3$, —CF$_2$CH$_3$. Halogen means F, Cl, Br, with F being preferred.

Preferred nonapeptides wherein Y is L-leucyl and X is an optically active D-form of selected amino acids and Z is NHC$_2$H$_5$ are [D-Trp$^6$, des-gly-NH$_2$$^{10}$]-LH-RH ethylamide . (X=D-Trp$^6$); [D-Ser-(t-BuO)$^6$, des-gly-NH$_2$$^{10}$]-LH-RH ethylamide [X=D-Ser(t-BuO$^6$)]; [D-Leu$^6$, des-gly-NH$_2$$^{10}$]-LH-RH ethylamide (X=D-Leu$^6$), [D-His(Bzl)$^6$, des-gly-NH$_2$$^{10}$]LH-RH ethylamide (X=iminobenzyl-D-His$^6$) and [D-Ala$^6$, des-gly-NH$_2$$^{10}$]-LH-RH ethylamide (X=D-Ala$^6$).

Preferred decapeptides include [D-Trp$^6$]-LH-RH wherein X=D-Trp, Y=L-leucyl, Z=glycyl-NH$_2$, [D-Phe$^6$]-LH-RH wherein X=D-phenylalanyl, Y=L-leucyl and Z=glycyl-HN$_2$) or [D-Nal(2)$^6$]LH-RH which is [(3-(2-naphthyl)-D-Ala$^6$]LH-RH wherein X=3-(2-naphthyl)-D-alanyl, Y=L-leucyl and Z=glycyl-NH$_2$.

Other LH-RH agonists useful within the scope of this invention are the $\alpha$-aza analogues of the natural LH-RH, especially, [D-Phe$^6$, Azgly$^{10}$]-LH-RH, [D-Tyr(-Me)$^6$, Azgly$^{10}$]-LH-RH, and [D-Ser-(t-BuO)$^6$, Azgly$^{10}$]-LH-RH disclosed by A. S. Dutta et al. in J. Med. Chem., 21, 1018 (1978) and U.S. Pat. No. 4,100,274 as well as those disclosed in U.S. Pat. Nos. 4,024,248 and 4,118,483.

Typical suitable LH-RH antagonists include [N-Ac-D-p-Cl-Phe$^{1,2}$, D-Phe$^3$, D-Arg$^6$, D-Ala$^{10}$]-LH-RH disclosed by J. Ercheggi et al., Biochem. Biophys. Res. Commun. 100, 915-920, (1981); [N-Ac-D-p-Cl-Phe[1,2], D-Trp[3], D-Arg[6], D-Ala[10]] LH-RH disclosed by D. H. Coy et al., Endocrinology, 110: 1445-1447, (1982); [N-Ac-D-(3-(2-naphthyl)-Ala)[1], D-p-Cl-Phe[2], D-Trp[3], D-hArg(Et$_2$)[6], D-Ala[10]]-LH-RH and [N-Ac-Pro[1], D-p-F-Phe[2], D-(3-(2-naphthyl)Ala[3,6]]-LH-RH disclosed by J. J. Nestor et al. J. Steroid Biochem., 20 (No. 6B), 1366 (1984); the nona- and decapeptide analogs of LH-RH useful as LH-RH antagonists disclosed in U.S. Pat. No. 4,481,190 (J. J. Nestor et al.); analogs of the highly constrained cyclic antagonist, cycle [$\Delta^3$ Pro[1], D-p-Cl-Phe[2], D-Trp[3,6], N-Me-Leu[7], $\beta$-Ala[10]]-LH-RH disclosed by J. Rivier, J. Steroid Biochem., 20, (No. 6B), 1365 (1984), and [N-Ac-D-(3-(2-naphthyl)-Ala[1], D-p-F-Phe[2], D-Trp[3], D-Arg[6]]-LH-RH disclosed by A. Corbin et al., J. Steroid Biochem. 20 (No. 6B) 1369 (1984).

Other LH-RH agonist and antagonist analogs are disclosed in *LH-RH and Its Analogs,* B. H. Vickory et al. editors at pages 3-10 (J. J. Nestor), 11-22 (J. Rivier et al.) and 23-33 (J. J. Nestor et al.)

The LH-RH agonists and antagonists useful in this invention may conveniently be prepared by the method described by Stewart et al. in "Solid Phase Peptide Synthesis" (published in 1969 by Freeman & Co., San Francisco, page 1) but solution phase synthesis may also be used.

The nona- and decapeptides used in this invention are conveniently assembled on a solid resin support, such as 1% cross-linked Pro-Merrifield resin by use of an automatic peptide synthesizer. Typically, side-chain protecting groups, well known to those in the peptide arts, are used during the dicyclohexylcarbodiimidecataylzed coupling of a tert-butyloxycarbonylamino acid to the growing peptide attached to a benzhydrylamine resin. The tert-butyloxycarbonyl protecting groups are removed at each stage with trifluoroacetic acid. The nona- or decapeptide is cleaved from the resin and deprotected by use of HF. The crude peptide is purified by the usual techniques, e.g., gel filtration and partition chromatography and optionally lyophilization. See also D. H. Coy et al., J. Med. Chem. 19, pages 423-425, (1976).

Typical suitable antiandrogens include nonsteroidal antiandrogens such as the imidazolidines, especially 1-(3'-trifluoromethyl-4'-nitrophenyl)-4,4-dimethyl-imidazoline-2,5-dione (also called Anandron) described in U.S. Pat. No. 4,097,578, or 4'-nitro-3'-trifluoromethylisobutyranilide (also called flutamide) described in U.S. Pat. No. 4,329,364 as well as the N-(phenylalkanoyl)aniline derivatives disclosed in U.S. Pat. No. 4,386,080 and the 3,4- disubstituted - branched - chain acylanilides disclosed in U.S. Pat. No. 4,239,776 (A. T. Glen et. al.). Flutamide is the preferred antiandrogen.

Typical suitable steroidal antiandrogens include 6-chloro-1,2-dihydro-17-(acetyloxy)-3'H-cyclopropa[1,2]pregna-1,4,6-triene-3,20-dione, available under the tradename of Androcur from Schering A. G., W. Berlin.

The inhibitors of sex steroid biosynthesis found useful in the present invention include those compounds which inhibit biosynthesis of sex steroids and precursor sex steroid especially those of adrenal and testicular origin.

Typical suitable inhibitors of sex steroid biosynthesis include 3-(4-aminophenyl)-3-ethyl-2,6-piperidinedione, an effective adrenal sex steroid biosynthesis inhibitor which is commonly called aminoglutethimide and is available from Ciba Pharmaceutical Co., Summit N.J. under tradename Cytadren and ketoconazole, an effective testicular but also adrenal sex steroid biosynthesis inhibitor which is available from Janssen Pharmaceutical, Piscataway, N.J. under the tradename Nizoral.

When an inhibitor of adrenal sex steroid biosynthesis, e.g., aminoglutethimide is administered in accordance with the present invention, cortisol biosynthesis is blocked. Accordingly, hydrocortisone is administered in physiological amounts sufficient to maintain normal glucocorticoid levels.

In this invention, the LH-RH agonist or antagonist and antiandrogen and inhibitor of sex steroid biosynthesis are administered as pharmaceutical compositions via topical, parenteral or oral means. The LH-RH agonist or antagonist is administered parenterally, i.e., intramuscularly, subcutaneously or intravenously by injection or infusion by nasal drops or by suppository. The LH-RH agonist or antagonist also may be microencapsulated in or attached to a biocompatible, biodegradable polymer, e.g., poly(d,l-lactide-co-glycolide) and subcutaneously or intramuscularly injected by a technique called subcutaneous or intramuscular depot to provide continuous, slow release of the LH-RH agonist or antagonist over a period of 30 days or longer. The most preferred route of administration of the LH-RH agonist or antagonist is subcutaneous depot injection. Preferably the antiandrogen will be administered orally. Preferably, the inhibitors of sex steroid biosynthesis such as aminoglutethimide and ketoconazole, when one or both are used in the present invention, are administered orally.

The amount of each component administered is determined by the attending clinicians taking into consideration the etiology and severity of the disease, the patient's condition and age, the potency of each component and other factors.

The LH-RH agonist or antagonist is generally administered at from about 10 to 5000 μg per day, with contemplated dosage ranges of about 10 to 1500 μg per day and about 250 to 500 μg per day for the LH-RH agonist and to about 50 to 5000 μg per day for the LH-RH antagonist being preferred.

In the most preferred embodiment of this invention, the LH-RH agonist or antagonist is administered subcutaneously in a daily dose of 500 μg for the first 30 days and thereafter subcutaneously in a daily dose of 250 μg regardless of the patients' body weight. When the LH-RH agonist or antagonist is administered, once every 30-day period or even longer, by intramuscular or subcutaneous depot injection, a dose from about 300 to 150,000 μg per 30-day period is used, with a dose of 750 to 15,000 μg per 30-day period being preferred.

The antiandrogen compositions are generally administered in a dosage range of about 0.20 to 40 mg/kg (body weight) per day with 750 mg per day in three equally divided doses being preferred.

The aminoglutethimide compositions when used are administered initially in a dosage of 250 mg given at 8-hour intervals and the dosage may be increased in increments of 250 mg daily up to a total daily dose of 2 grams.

The ketoconazole compositions when used are administered orally in a dose of 250 mg given at 8-hour intervals and the dosage may be increased to a daily dose of 2 grams.

The LH-RH agonist or antagonist and antiandrogen and inhibitor of sex steroid biosynthesis each may be administered separately or when the modes of administration are the same, all or two of them may be administered in the same composition, but in any case the preferred ratio of LH-RH agonist to antiandrogen to inhibitor of sex steroid biosynthesis administered daily will be about 250 µg of LH-RH agonist to about 750 mg of antiandrogen to about 750 mg of inhibitor of sex steroid biosynthesis.

In the most preferred aspect of this invention, the LH-RH agonist is [D-Trp$^6$, des-Gly NH$_2^{10}$]LH-RH ethylamide which is administered subcutaneously in single daily dose of 500 µg for the first thirty (30) days of treatment and thereafter in a single daily dose of 250 µg; the antiandrogen is 4'-nitro-3'-trifluoromethylisobutyranilide, i.e., flutamide, which is administered orally in three equally divided daily doses of 250 m; and the inhibitor of sex steroid biosynthesis is ketoconazole alone or in association with aminoglutethimide, each of which is administered orally in three equally divided doses of 250 mg every 8 hours.

The inhibitor(s) of sex steroid biosynthesis and the antiandrogen are preferably administered to a male in need of the prostate cancer treatment of this invention one or two days before the LH-RH agonist or antagonist is administered, but the attending clinician may elect to start administration of the LH-RH agonist or antagonist, the antiandrogen and the inhibitor of steroid biosynthesis on the first day of the treatment.

When patients whose testes have already been surgically removed are treated according to this invention, the antiandrogen administration and dosage are the same as indicated when the antiandrogen is used in combination with the LH-RH agonist or antagonist as well as the third ingredient, i.e. the inhibitor of adrenal sex steroid biosynthesis such as aminoglutethimide. Normally, an inhibitor of testicular sex steroid biosynthesis such as ketoconazole may be administered to chemically but not surgically castrated patients.

Generally, the inhibitor of testicular sex steroid biosynthesis, e.g., ketoconazole will be administered until the serum levels of T and DHT stimulated by the administration of the LH-RH agonist are effectively suppressed, normally for one to three weeks. The inhibitor of adrenal sex steroid biosynthesis, e.g., aminoglutethimide may be administered at the start of treatment in the presence or absence of the inhibitor of testicular sex steroid biosynthesis and thereafter continued throughout the period of treatment.

The LH-RH agonists or antagonists useful in the present invention are typically amorphous solids which are freely soluble in water or dilute acids, e.g., HCl, H$_2$SO$_4$, citric, acetic, mandelic or fumaric. The LH-RH agonist or antagonist for subcutaneous injection is supplied in vials containing 6 mL of sterile solution with the LH-RH agonist or antagonist at a concentration of about 1.0 mg/mL.

A typical pharmaceutical composition of the LH-RH agonists or antagonists include the LH-RH agonist or antagonist or a pharmaceutically acceptable acid salt thereof, benzyl alcohol, a phosphate buffer (pH=6.9-7.2) and sterile water.

The LH-RH agonist or antagonist for intramuscular or subcutaneous depot injection maybe microencapsulated in a biocompatible, biodegradable polymer, e.g., poly (d,1-lactide-co-glycolide) by a phase separation process or formed into a pellet. The microspheres may then be suspended in a carrier to provide an injectable preparation or the depot may be injected in the form of a pellet.

The aminoglutethimide and ketoconazole are typically compounded in customary ways for oral administration, e.g., in tablets, capsules and the like.

The antiandrogens useful in the present invention are typically formulated with conventional pharmaceutical excipients, e.g., spray dried lactose and magnesium stearate into tablets or capsules for oral administration. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, tasteimproving substances can be added in the case of oraladministration forms.

As further forms of administration, one can use plug capsules, e.g., of hard gelatin, as well as closed soft-gelatin capsules comprising a softner or plasticizer, e.g., glycerine. The plug capsules contain the active substance preferably in the form of granulate, e.g., in mixture with fillers, such as lactose, saccharose, mannitol, starches, such as potato starch or amylopectin, cellulose derivatives or highly-dispersed silicic acids. In softgelatin capsules, the active substance is preferably dissolved or suspended in suitable liquids, such as vegetable oils or liquid polyethylene glycols.

In place of oral administration, the active compounds may be administered parenterally. In such case, one can use a solution of the active substance, e.g., in sesame oil or olive oil.

Following the above treatment using the described regimen, prostate carcinoma growth and bone metastases are inhibited and in some instances complete remission occurs.

What is claimed:

1. A method of treating prostate cancer in a warm-blooded male animal in need of such treatment which comprises blocking the testicular hormonal secretions of said animal by surgical or chemical means and administering to said animal therapeutically effective amounts of an antiandrogen in association with at least one inhibitor of sex steroid biosynthesis, or pharmaceutical compositions thereof.

2. The method of claim 1 wherein the testes are surgically removed and an inhibitor of adrenal sex steroid biosynthesis is administered in association with an antiandrogen or pharmaceutical compositions thereof.

3. The method of claim 1 wherein the testicular hormonal secretions are blocked by administering an amount of a LH-RH agonist or a LH-RH antagonist or a pharmaceutical composition thereof effective to block said hormonal secretions.

4. The method according to claim 3 wherein the LH-RH agonist or the LH-RH antagonist is administered parenterally together with a pharmaceutically acceptable parenteral carrier.

5. The method of claim 3 wherein one inhibitor of sex steroid biosynthesis or a pharmaceutical composition thereof is administered.

6. The method of claim 5 wherein the inhibitor of sex steroid biosynthesis is ketoconazole or a pharmaceutical composition thereof.

7. The method of claim 5 wherein two inhibitors of sex steroid biosynthesis or pharmaceutical compositions thereof are administered.

8. The method of claim 7 wherein the two inhibitors of sex steroid biosynthesis are aminoglutethimide and ketoconazole or pharmaceutical compositions thereof.

9. The method of claim 1 wherein the antiandrogen and the inhibitor or inhibitors of steroid biosynthesis are each administered orally, together with a pharmaceutically acceptable oral carrier.

10. The method of claim 1 wherein the LH-RH agonist is a nonapeptide or a decapeptide represented by the formula: L-pyroglutamyl-L-histidyl-L-tryptophyl-L-seryl-L-tyrosyl-X-Y-L-arginyl-L-prolyl-Z, wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanlyl or N-methyl-D-alanyl and wherein Y is L-leucyl, $N^\alpha$-methyl-L-leucyl, D-leucyl $N^\alpha$-methyl-D-leucyl, or D-alanyl and wherein Z is glycyl-$NHR_1$ or $NHR_1$ wherein $R_1$ is H, lower alkyl or haloloweralkyl.

11. The method of claim 1 wherein the antiandrogen is 1-(3'-trifluoromethyl-4'-nitrophenyl)-4,4-dimethylimidazoline-2,5-dione.

12. The method of claim 1 wherein the antiandrogen is 4'-nitro-3'-trifluoromethylisobutyranilide.

13. A method of treating prostate cancer in a castrated warm-blooded male animal which comprises administering to said animal a therapeutically effective amount of an association of an antiandrogen and at least one inhibitor of sex steroid biosynthesis, or pharmaceutical compositions thereof.

14. The method of claim 13 wherein one inhibitor of sex steroid biosynthesis or a pharmaceutical composition thereof is administered.

15. The method of claim 14 wherein the inhibitor of sex steroid biosynthesis is ketoconazole or a pharmaceutical composition thereof.

16. The method of claim 14 wherein the inhibitor of sex steroid biosynthesis is aminoglutethimide or a pharmaceutical composition thereof.

17. The method of claim 13 wherein two inhibitors of sex steroid biosynthesis or pharmaceutical composition thereof are administered.

18. The method of claim 17 wherein the two inhibitors of sex steroid biosynthesis are aminoglutethimide and ketoconazole or pharmaceutical compositions thereof.

19. The method of claim 13 wherein the antiandrogen and the inhibitor or inhibitors of sex steroid biosynthesis are each administered orally, together with a pharmaceutically acceptable oral carrier.

20. The method of claim 13 wherein the antiandrogen is 1-(3'-trifluoromethyl-4'-nitrophenyl)-4,4-dimethylimidazoline-2,5-dione.

21. The method of claim 13 wherein the antiandrogen is 4'-nitro-3'-trifluoromethylisobutyranilide.

22. A method of treating prostate cancer in a warm-blooded male animal having prostate cancer which comprises administering to said animal therapeutically effective amounts of a LH-RH agonist or a LH-RH antagonist in association with an antiandrogen and at least one inhibitor of sex steroid biosynthesis or pharmaceutical compositions thereof.

23. The method of claim 22 wherein the LH-RH agonist is administered parenterally together with a pharmaceutically acceptable parenteral carrier.

24. The method of claim 22 wherein the inhibitor or inhibitors of sex steroid biosynthesis and the antiandrogen are each administered orally, together with a pharmaceutically acceptable oral carrier.

25. The method of claim 22 wherein the LH-RH agonist is administered at a daily parenteral dose of between about 250 and 500 μg.

26. The method of claim 22 wherein the antiandrogen is administered at a daily oral dose of between about 0.20 and 40 mg/kg and the inhibitor of steroid biosynthesis is administered at a daily oral dose of between about 0.20 and 40 mg/kg.

27. The method of claim 22 wherein one inhibitor of sex steroid biosynthesis or a pharmaceutical composition thereof is administered.

28. The method of claim 27 wherein the inhibitor of sex steroid biosynthesis is ketoconazole or a pharmaceutical composition thereof.

29. The method of claim 27 wherein the inhibitor of sex steroid biosynthesis is aminoglutethimide or a pharmaceutical composition thereof.

30. The method of claim 22 wherein two inhibitors of sex steroid biosynthesis or pharmaceutical compositions thereof are administered.

31. The method of claim 30 wherein the two inhibitors of sex steroid biosynthesis are aminoglutethimide and ketoconazole or pharmaceutical compositions thereof.

32. A method of claim 29 which further comprises administering a physiological amount of hydrocortisone sufficient to maintain normal glucocorticoid levels.

33. A kit comprising in separate containers pharmaceutical compositions for combined use in treating prostate cancer which comprises (1) a pharmaceutical composition comprising an antiandrogen (2) a pharmaceutical composition comprising a LH-RH agonist or antagonist and (3) a sex steroid biosynthesis inhibitor oral pharmaceutical composition.

34. The kit of claim 33 wherein an adrenal sex steroid biosynthesis inhibitor is used.

35. The kit of claim 33 wherein a testicular sex steroid biosynthesis inhibitor is used.

36. The kit of claim 35 wherein the testicular sex steroid inhibitor is ketoconazole.

37. A kit comprising in separate containers pharmaceutical compositions for combined use in treating prostate cancesr which comprises (1) a pharmaceutical composition comprising a LH-RH agonist or a LH-RH antagonist (2) a pharmaceutical composition comprising an inhibitor of adrenal sex steroid formation and (4) a pharmaceutical composition comprising hydrocortisone.

38. The kit of claim 37 wherein the pharmaceutical compositions are oral compositions.

39. The kit of claim 37 wherein the LH-RH agonist pharmaceutical composition comprises the LH-RH agonist in one container and a solvent for parenteral administration in another container.

40. The kit of claim 37 wherein the pharmaceutical compositions of the antiandrogen, the hydrocortisone and the inhibitor of adrenal sex steroid formation are each oral compositions.

41. A kit comprising in separate containers pharmaceutical composition for combined use in treating prostate cancer which comprises (1) a pharmaceutical composition comprising a LH-RH agonist or a LH-RH antagonist (2) a pharmaceutical composition comprising an antiandrogen (3) a pharmaceutical composition comprising an inhibitor of testicular sex steroid biosynthesis (4) a pharmaceutical composition an inhibitor of adrenal sex steroid biosynthesis and (5) a pharmaceutical composition comprising hydrocortisone.

42. A method of claim 22 wherein the LH-RH agonist or LH-RH antagonist is administered at a daily dose of between about 10 and 5000 μg.

43. A method of claim 22 wherein the LH-RH agonist is administered at a daily dose of between about 10 and 1500 μg.

44. A method of claim 22 wherein the LH-RH antagonist is administered at a daily dose of between about 50 to 5000 μg.

* * * * *